(12) United States Patent
Such et al.

(10) Patent No.: US 8,315,682 B2
(45) Date of Patent: Nov. 20, 2012

(54) INTEGRATED PULSE OXIMETRY SENSOR

(75) Inventors: Olaf Such, Aachen (DE); Josef Lauter, Geilenkirchen (DE); Robert Pinter, Aachen (DE); Jens Muehlsteff, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1559 days.

(21) Appl. No.: 11/720,887

(22) PCT Filed: Dec. 5, 2005

(86) PCT No.: PCT/IB2005/054065
§ 371 (c)(1),
(2), (4) Date: Jun. 5, 2007

(87) PCT Pub. No.: WO2006/064399
PCT Pub. Date: Jun. 22, 2006

(65) Prior Publication Data
US 2009/0240125 A1 Sep. 24, 2009

Related U.S. Application Data

(60) Provisional application No. 60/635,985, filed on Dec. 14, 2004.

(51) Int. Cl.
*A61B 5/1455* (2006.01)
(52) U.S. Cl. ........................ 600/323; 600/310
(58) Field of Classification Search ........... 600/309–344
See application file for complete search history.

(56) References Cited

U.S. PATENT DOCUMENTS

| 5,203,342 | A | 4/1993 | Sakai |
| 5,490,523 | A * | 2/1996 | Isaacson et al. ............... 600/323 |
| 5,921,921 | A | 7/1999 | Potratz et al. |
| 6,292,528 | B1 | 9/2001 | Wieczorek et al. |
| 6,496,711 | B1 | 12/2002 | Athan et al. |
| 6,501,973 | B1 * | 12/2002 | Foley et al. .................... 600/310 |
| 6,597,025 | B2 | 7/2003 | Lauter et al. |
| 6,898,451 | B2 * | 5/2005 | Wuori ............................ 600/322 |
| 2003/0163033 | A1 | 8/2003 | Dekker |
| 2004/0087845 | A1 * | 5/2004 | Katarow et al. ............... 600/323 |
| 2004/0108525 | A1 * | 6/2004 | Sekine ........................... 257/202 |

* cited by examiner

Primary Examiner — Eric Winakur
Assistant Examiner — Marjan Fardanesh

(57) ABSTRACT

In a medical pulse oximetry sensor (10) at least two light emitting diodes (16, 18) are disposed to emit red light and infrared light through a portion of a subject's anatomy with a typically high oxygenated blood throughput. Typically, this area is also relatively narrow, to allow the light to pass through the area with acceptable attenuation, such as a finger or an earlobe. Light emitted from the LEDs (16, 18) is incumbent upon an integrated circuit (22) printed from a single CMOS substrate (21). The integrated circuit (22) includes all preprocessing and post-processing elements needed to convert the detected light signals into a pulse oximetry measurement. These elements include a photodetector (20), a photo pre-amplifier (40), a sampler/holder (42), an analog to digital converter (44), a microprocessor (46) a rangefinder (48), a timing control circuit (50) and an LED control circuit (52). By integrating all pre and post processing functions into the carriage housing (12), the system becomes more efficient, less expensive to manufacture, and more robust to ambient light and x-ray radiation.

18 Claims, 4 Drawing Sheets

INTEGRATED PULSE OXIMETRY SENSOR

CROSS REFERENCE TO RELATED APPLICATIONS

This application claims the benefit of U.S. provisional application Ser. No. 60/635,985 filed Dec. 14, 2004, which is incorporated herein by reference.

The present invention relates to measurement of patient pulse oximetry, that is, the measure of the amount of Oxygen in a patient's blood.

$SpO_2$, an abbreviation used for pulse oximetry, is a method that is widely accepted in the medical world to measure the content of oxygen in the arterial blood by means of light. Typically, $SpO_2$ sensors include light emitting diodes (LEDs) that shine red and infrared light through the tissue. Most sensors are used at relatively narrow extremities, such as a finger, toe, or ear. The blood bone and tissue at the measurement site absorb much of the incident light, but sufficient light traverses the tissue to be useful for measurement. Typically, a light sensitive detector such as a photodiode opposite the source receives the light that passes through the extremity.

The sensor measures the amount of red and infrared light received by the detector and calculates the amount of each wavelength absorbed. The amounts of light absorbed by tissue, bone, and venous blood do not change dramatically over short periods of time. The amount of arterial blood does change over short periods of time due to natural pulsation of the extremity, but because it is the only variable that is changing over short periods of time, it can be isolated from the other components.

The amount of light received by the detector indicates the amount of oxygen bound to hemoglobin in the blood. Oxygenated hemoglobin ($HbO_2$) absorbs more infrared light than red light. Deoxygenated hemoglobin (Hb) absorbs more red light than infrared light. By comparing the amounts of red and infrared light received, the instrument can calculate the $SpO_2$ reading of the blood.

Due to the amount of surrounding ambient light sources that overlay the useful signal, it is necessary to modulate and demodulate the light from the two LEDs. Currently, a standard pulse oximetry sensor includes a passive photodiode packaged into a finger clip or similar housing together with the LEDs. The modulation/demodulation of the light source and the amplification filtering and processing of the signal is then typically done on a printed circuit board remote from the actual sensor, typically with a relatively long, high impedance cable connecting the systems.

Multiple disadvantages are inherent with such a system. Typical current designs are costly, consume significant power, and are relatively bulky. Current picosat boards typically in use consume 200 mW of power and the board alone has a volume of 30 cm and costs about $110 without the sensor. Wireless use is impracticable for both power consumption reasons and size/weight reasons. Further, the cost makes it impracticable for personal health care type products.

In addition to size/cost restraints, the separation of the amplifier and photodiode forces the system to run a small photocurrent through the high impedance long cable to the preamplifier. This setup complicates the matter due to shielding requirements and crosstalk issues.

The present application contemplates a new and improved pulse oximetry monitoring system for use in conjunction with units capable of both wired and wireless communication, which overcomes the above-referenced problems of size, cost, and outsourcing issues, and others.

In accordance with one aspect of the present invention, a medical pulse oximetry sensor is provided. A carriage housing houses first and second light emitting diodes, one emitting light in the red spectrum, and the other emitting light in the infrared spectrum. A photodiode detects incumbent light from the first and second light emitting diodes after the emitted light has passed through a blood oxygenated portion of a subject. Electrical signals are generated. A processing circuit integrally formed on an integrated semiconducting component chip mounted in the carriage housing processes the signals into a pulse oximetry value.

In accordance with another aspect of the present invention, a method of manufacturing a pulse oximetry sensor is provided. At least first and second light emitting diodes are embedded into a carriage housing. An integrated circuit is embedded in the housing opposite the light emitting diodes such that light emitted by the diodes must pass through the portion of the subject's anatomy before impinging upon the integrated circuit. The integrated circuit includes at least one photodiode for detection of light signals from the at least two light emitting diodes and generating signals indicative thereof. The circuit also includes an amplifier for amplifying the signals from the photodiode. The circuit includes digital conversion elements for digitizing the signals from the photodiode. Also the circuit includes a processing unit for processing the digital signals into the pulse oximetry value.

In accordance with another aspect of the present invention, a method of measuring blood oxygen is provided. Pulses of red light are emitted from a first LED mounted in a carriage housing adapted to fit snugly about a portion of a subject's anatomy with a relatively high oxygenated blood throughput. Pulses of infrared light are emitted from a second LED also mounted in the carriage housing. Light from the LEDs is received which has traversed a blood oxygenated portion of a person with a photodiode mounted in the carriage housing. The photodiode generates electrical signals. The signals are processed into a blood oximetry value with a processing circuit integrally formed on a semiconductor chip that is mounted in the carriage housing.

One advantage of the present invention resides in its small size.

Another advantage resides in the close proximity of detection elements and signal conditioning, which gives better noise performance and eliminates expensive wiring.

Another advantage resides in the separation of special functions in different semiconductor processes which leads to top overall performance for all parts of the system.

Another advantage resides in independent testability of all subsystems of the sensor.

Another advantage resides in smaller and more specialized subsystems that can be produced with a higher yield.

Another advantage resides in increased automation in processing.

Another advantage resides in low cost.

Another advantage resides in significant reduction in direct weight of the sensor.

Another advantage resides in reduced power consumption.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
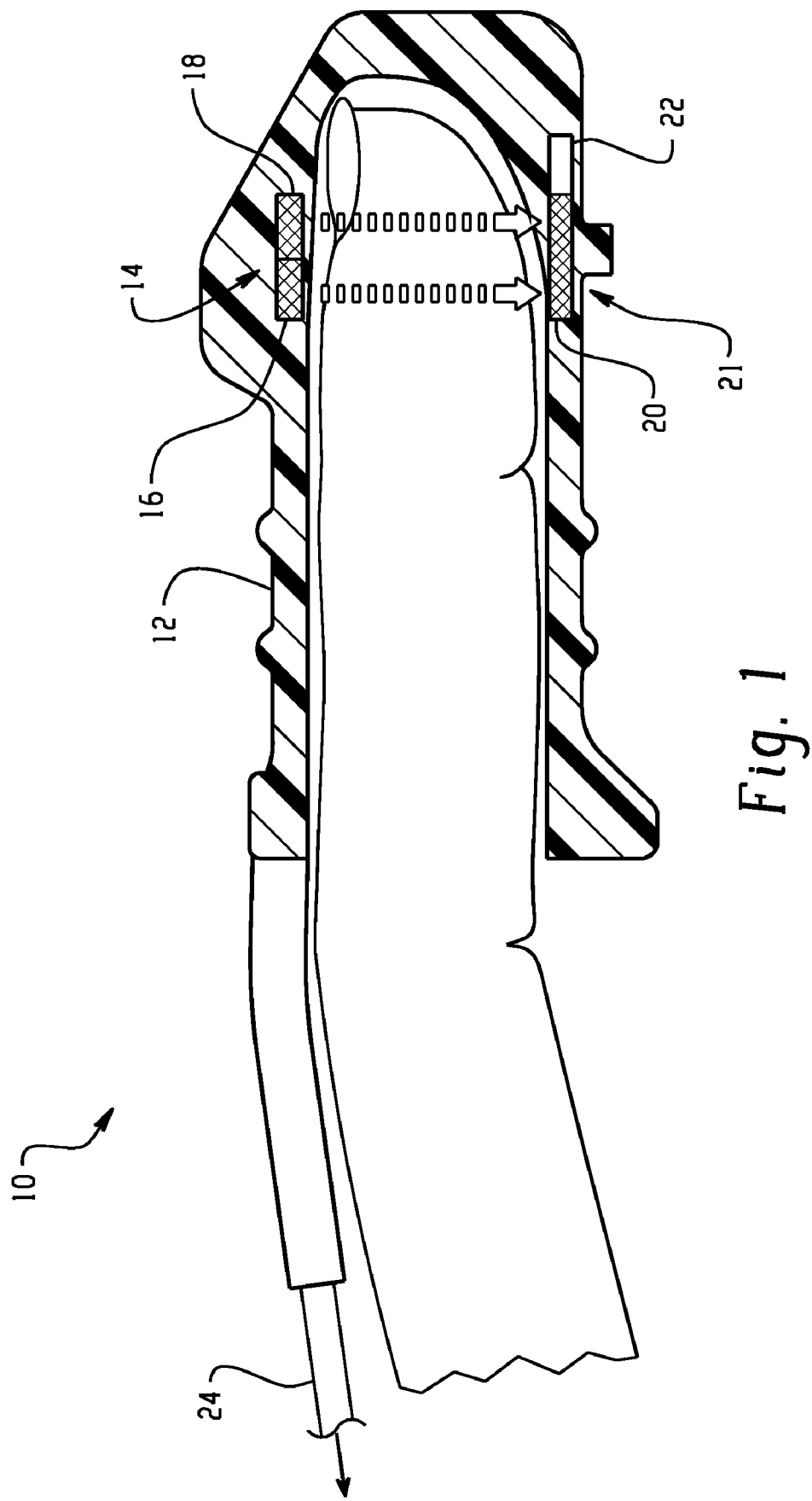
FIG. 1 is an illustration of a preferred implementation of a wired medical pulse oximetry sensor with integrated processing in the finger unit.

With reference to FIG. 1, a preferred medical pulse oximetry sensor 10 is illustrated. Typically, the sensor 10 is adapted to fit over the finger of a subject, but it is to be understood that the sensor 10 could be easily adapted to accommodate alternate sites that have relatively good blood oxygenated throughput, and are sufficiently light translucent, such as the toe or the earlobe. The sensor 10 includes a housing 12 which fits snugly around the anatomy in question, so as to keep the sensor 10 from falling off of the anatomy, but not so snug as to prevent circulation of blood therein.

The preferred sensor includes a light emitting array 14 which in the illustrated embodiment, includes two light emitting diodes 16, 18. Diode 16, when stimulated emits light from the visible red wavelength of the electromagnetic spectrum, and the diode 18, when stimulated emits light from the infrared portion of the electromagnetic spectrum. It is to be understood that a plurality of additional wavelengths can be used in conjunction with, or in lieu of the two types of light illustrated in FIG. 1. As many as ten or more different wavelengths could be utilized in a preferred embodiment of the pulse oximetry sensor according to the present application.

With continuing reference to FIG. 1, following the arrows from the light emitting diodes 16, 18 and through the depicted finger, there is a photoreceptor array 20. This array preferably includes a photodiode capable of being stimulated by at least the red and infrared spectra, but as noted previously, compatibility with many more wavelengths is preferable. Immediately adjacent the photoreceptor array 20, preferably on a common CMOS chip 21, resides signal processing electronics 22 of the preferred pulse oximetry sensor 10. Depicted in FIG. 1 as an extension of the photoreceptor array 20 for the sake of clarity, it is to be understood that the signal processing electronics 22 can be located anywhere adjacent to the photoreceptor array 20, but is most preferably integrated with the photoreceptor array 20. The photodiode is preferably integrally formed on the same CMOS chip as the electronic components 22 described in detail below. However, it is contemplated that the photodiode can be formed separately from the CMOS chip 21, bonded or otherwise electrically connected to it. A data transmission cable 24 is attached to the housing 12 to transport the analyzed pulse oximetry data to a typical means of display or recordation and to provide power to the components of the pulse oximetry sensor. Because the data has been processed, preferably digitized, and amplified, the transmission cable need not be shielded and can be low impedance.

Figure 2:
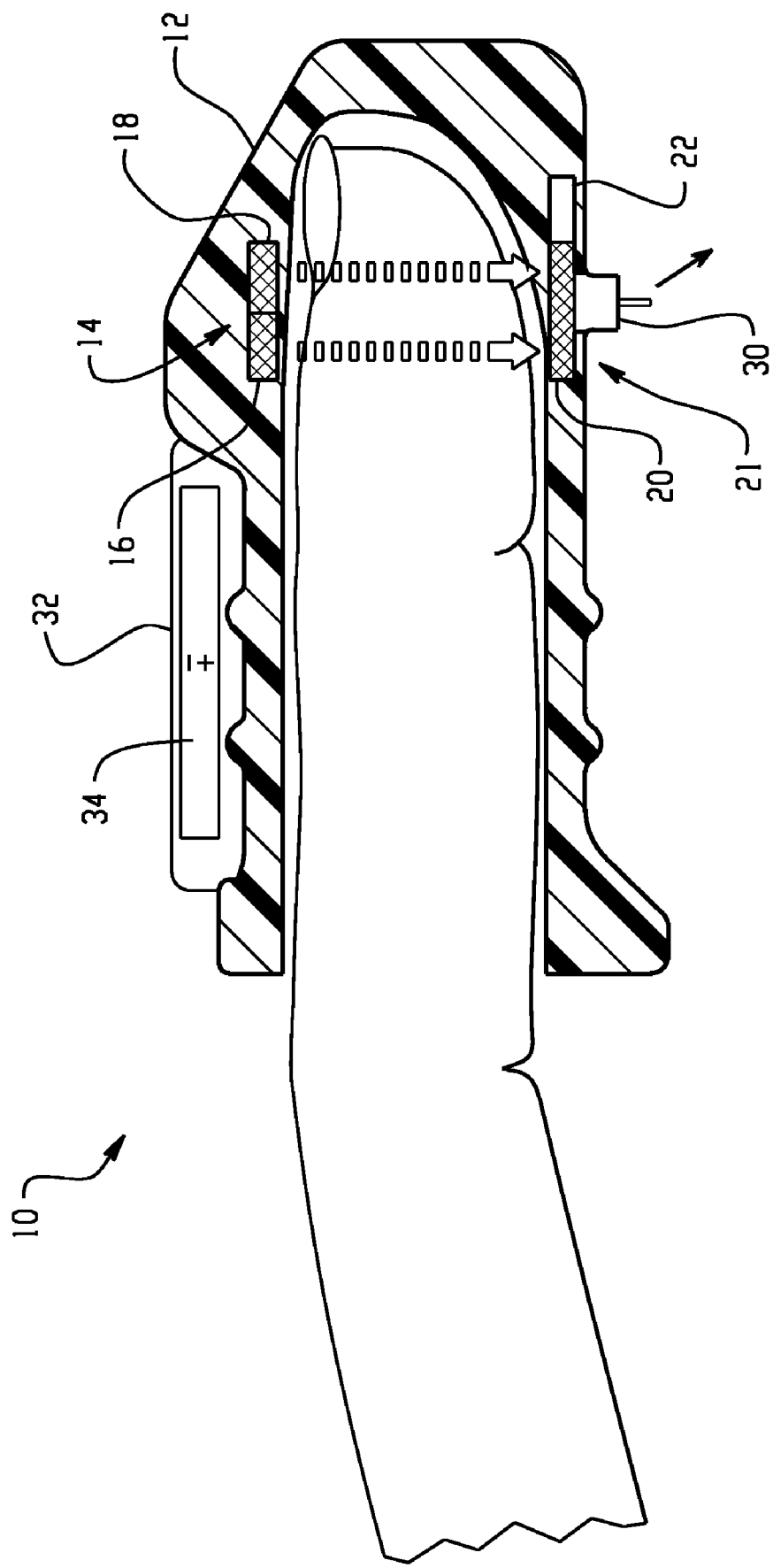
FIG. 2 is an illustration of a preferred implementation of a wireless embodiment of the medical pulse oximetry sensor of FIG. 1.

With reference now to FIG. 2, a wireless embodiment of the pulse oximetry sensor 10 is depicted. It is to be understood that the functional discussion that applies to FIG. 1 also applies to FIG. 2, inasmuch as like indicators indicate like components. Most significant differences, of course, are an on-board power supply, a wireless transmitter/receiver, and the lack of a connecting power/data transmission cable. Functionally, the pulse oximetry sensor depicted in FIG. 1 is operationally very similar to the wireless embodiment depicted in FIG. 2.

A wireless transmitter 30 transmits the analyzed pulse oximetry data from the CMOS chip 21 to a remote console for viewing. The transmitter is preferably a Bluetooth™ type transmitter because it is a power and processing efficient format and because shorter range transmissions are preferred. The transmitter is relatively short range, preferably transmitting to a console within the subject's room, and not reaching the consoles of similar units in other parts of the medical facility. More powerful and longer range transmitters are also contemplated, such as RF embodiments, where appropriate. Preferably, the transmitter/receiver is a separate chip from the signal processing electronics 22, as opposed to integrated within the electronics chip 21. Optionally, the wireless transmitter 30 is a transceiver for receiving post processing and control instructions and the like from a dedicated host system. Such messages or indicators could be battery status monitoring messages, on/off commands, encryption codes, processing instructions, and the like. In the preferred embodiment, the transmitter 30 is located adjacent to the integrated processing electronics 22, but it is to be understood that the transmitter may be also integrated into the CMOS chip 21 that houses the signal processing electronics 22 or located in a more remote portion of the sensor assembly.

The wireless embodiment includes an on-board power supply housing 32 wherein is located a power supply, preferably a battery 34. The battery 34 is preferably a lithium-ion battery. The battery 34 is the most bulky component of the wireless pulse oximetry embodiment, so a balance is desired between battery life and bulk. In a hospital environment, it is conceivable that battery lives of a ½ day or a day are acceptable. Rechargeable batteries could be recharged periodically on convenient in-room battery chargers designed to receive the pulse oximetry sensors that are not in use. If, however, longer battery lives are desired, for such applications as home use or extended hospital stays, larger (such as a AA or AAA cell) are possible. Other power supplies such as solar cells, other charge storage devices, inductive couplings, and the like are also contemplated.

Figure 3:
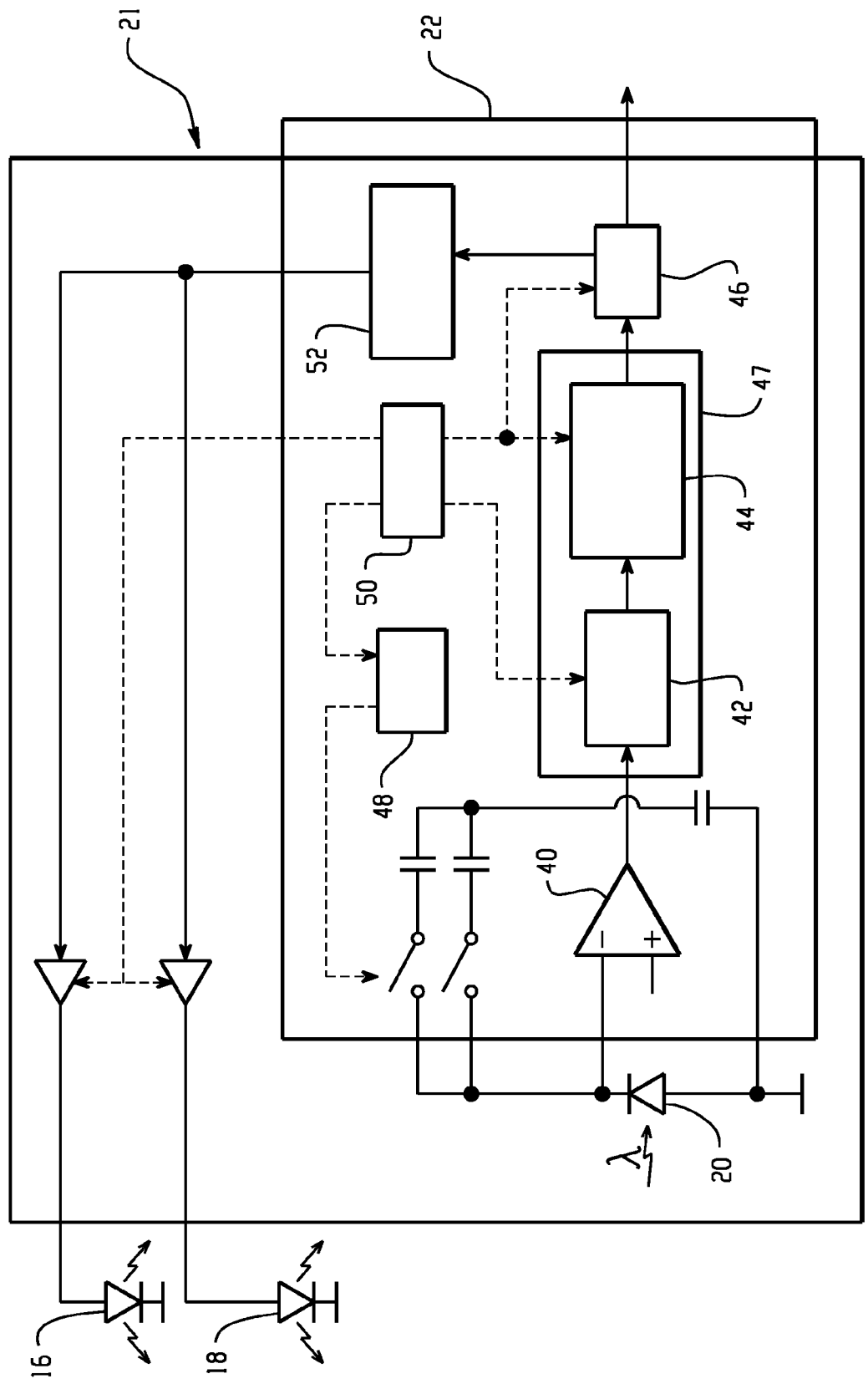
FIG. 3 is a circuit diagram, of the integrated circuitry of the pulse oximetry sensors of FIGS. 1 and 2.

Now with reference to FIG. 3, the processing electronics 22 are depicted in greater detail. All of the components are 22 integrated into a single CMOS chip 21. Integrated design enables significant reduction of size, cost, direct weight of the sensor, reduction of power consumption, and thus further reduction of other components and parameters due to shrinking the power supply. The disclosed embodiment reduces the production cost of an $SpO_2$ sensor including demodulation, filtering, and pre-processing, LED control and drivers to be comparable with the current cost of the photodiode and finger mounting assembly.

The first component integrated is the photoreceptor array 20. As discussed previously, the photoreceptor array receives light data from the red emitting diode 16 and the infrared emitting diode 18. These signals are immediately amplified by an attached photo preamplifier 40. With no cable to traverse between the photodiode and the amplifier, amplification is performed before the light signals undergo significant attenuation or acquire significant background noise. The amplified signals are sampled and held by a sample/hold 42 until an iteration of each wavelength has been sampled (two in the preferred embodiment, but as many as is practically allowable, such as ten as discussed previously) including a reference (dark) channel in which no light is emitted. The dark channel is sampled to provide a reference so that the system can create a baseline and cancel out any ambient light contribution and exclude it from the pulse oximetry measurement. The individual wavelength signals are then separately digitized by an analog to digital converter 44, and passed to a microprocessor 46 (CPU) of the integrated electronics 22. Optionally, the sample/hold 42 and the analog to digital converter 44 are combined into a Sigma Delta (ΣΔ) converter 47, combining the holding and digitizing into a single step.

The flow of samples is filtered digitally by the CPU 46 and adjusted according to intensity based on detected light levels. To aid the CPU 46 in adjusting the intensities of the signals, a dynamic rangefinder 48 is included to compensate for different measurement sites, (e.g. finger vs. earlobe) LED efficiencies, skin color/tone, and the like. Information from the rangefinder 48 is fed back into preamplifier 40 to be used in the next iteration of detected LED emissions.

A timing circuit 50 coordinates the rangefinder 48, the lighting of the LEDs 16, 18, and the processing and hold of data through the sample 42, the A/D converter 44 and the CPU 46. In the preferred embodiment, the timing circuit 50 coordinates alternating bursts from the diodes 16, 18 and dark channels on the order of 1 KHz iterations, e.g., every millisecond. This value is chosen to be well above the frequency of most ambient light sources (e.g. florescent) and in this manner, may be as small as about 250 Hz. At slower switching speeds, the pauses between light emissions are longer to avoid prematurely burning out the LEDs 16, 18. The CPU 46 guided by the timing circuit 50 coordinates with an LED controller 52 for precise lighting of the LEDs 16, 18. After receiving iterations of the detected light, the CPU 46 translates the detected light signals into a pulse oximetry measurement. The updated pulse oximetry measurement is then passed on from the CPU 46 to a suitable display via the cable 24, (as per FIG. 1) or via the transmitter 30 (as per FIG. 2).

Figure 4:
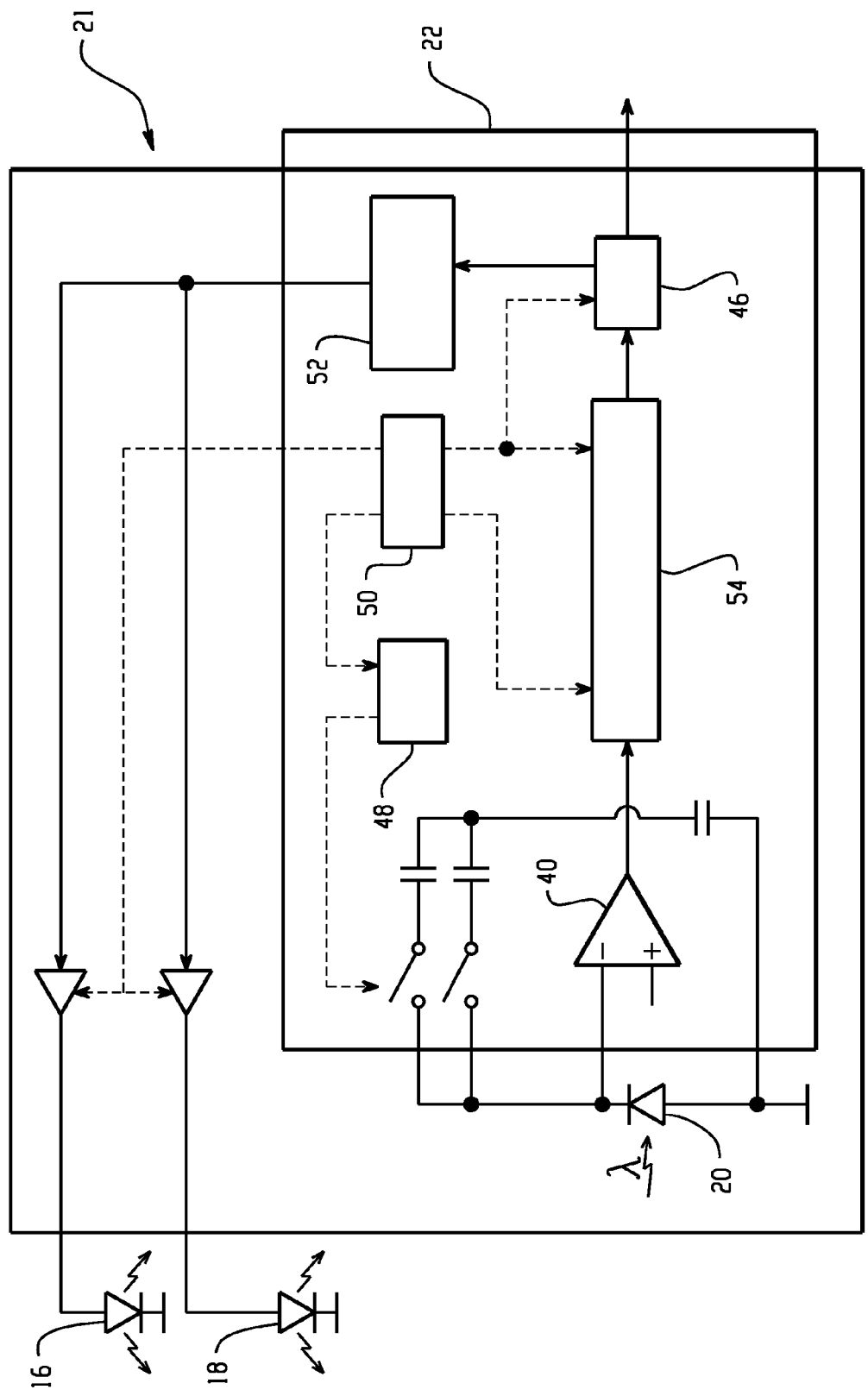
FIG. 4 depicts an alternate embodiment of the circuit shown in FIG. 3.

In an alternate embodiment, as shown in FIG. 4 the use of a current to voltage converter 54 instead of the sample/hold 42, ADC 44 combination is contemplated. This alternate embodiment may be used for analog modulation schemes such as frequency or phase multiplexed LED modulation.

Also alternatively, multiple parallel sample/holds 42 and ADCs 44 can be added to relax requirements on the single ADC 44 processing channel. Analog or hardwired digital filters and demodulation can also be used in this concept.

Also alternatively, it is contemplated that the red and infrared signals received from the light emitting diodes be converted into plethysmographic waveforms from at least one of the red and infra-red spectra/

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A medical pulse oximetry sensor comprising:
   a carriage housing adapted to fit snugly about a portion of a subject's anatomy with a relatively high oxygenated blood throughput;
   a first light emitting diode mounted in the housing for emitting light in the electromagnetic spectrum of the red wavelengths;
   a second light emitting diode mounted in the housing for emitting light in the electromagnetic spectrum of the infrared wavelengths;
   an integrated CMOS semiconducting component chip mounted in the carriage housing which includes:
   at least one photodiode for detecting incumbent light from the first and second light emitting diodes after the emitted light has passed through a blood oxygenated portion of a subject and generating electrical signals indicative thereof;
   an amplifier for amplifying the signal from the at least one photodiode;
   a microprocessing unit for processing the amplified signals into at least one of pulse oximetry value and plethymographic waveforms;
   a light emitting diode control operationally connected to the microprocessing unit that controls light emissions from the first and second light emitting diodes; and
   a timing circuit that coordinates processing the signals generated by the photodiode and operations of the light emitting diodes.

2. The medical pulse oximetry sensor as set forth in claim 1, wherein the CMOS semiconducting chip further includes:
   a sigma delta modulator for sampling the amplified signals and converting the signals into digital format.

3. The medical pulse oximetry sensor as set forth in claim 2, wherein the CMOS semiconducting chip further includes:
   a sample and hold operatively connected to the amplifier for sampling and holding the amplified signals.

4. The medical pulse oximetry sensor as set forth in claim 3, wherein the CMOS semiconducting chip further includes:
   an analog to digital converter for digitizing sampled and held amplified signals.

5. The medical pulse oximetry sensor as set forth in claim 1, wherein the CMOS semiconducting chip further includes:
   a current to voltage converter for analog modulation and one of frequency and phase multiplexed LED modulation of the signals from the photodiode.

6. The medical pulse oximetry sensor as set forth in claim 1, wherein the CMOS semiconducting chip further includes:
   a range finder that selects an amplification range for the amplifier to adjust signal intensities in accordance with characteristics of a measurement site, photodiode efficiency and/or skin color/tone.

7. The medical pulse oximetry sensor as set forth in claim 1, further including:
   additional light emitting diodes, each emitting additional wavelengths of electromagnetic radiation.

8. The medical pulse oximetry sensor as set forth in claim 1, wherein the photodiode is integrally formed in the CMOS semiconductor chip.

9. The medical pulse oximetry sensor as set forth in claim 1, further including:
   a wireless transmitter for transmitting the calculated pulse oximetry value to at least one of a display console and a data recordation device; and
   a battery for providing power to the pulse oximetry sensor.

10. The medical pulse oximetry sensor as set forth in claim 9, wherein the wireless transmitter controls processing the on/off command for the oximetry sensor.

11. The medical pulse oximetry sensor as set forth in claim 9, wherein the wireless transmitter is formed on a separate chip.

12. The medical pulse oximetry sensor as set forth in claim 1, further including:
   a cable for providing power to the pulse oximetry sensor and for transmitting the calculated pulse oximetry value to at least one of a display console and a recordation device.

13. A method of measuring blood oxygen comprising:
   emitting pulses of red light from a first LED mounted in a carriage housing adapted to fit snugly about a portion of a subject's anatomy with a relatively high oxygenated blood throughput;

emitting pulses of infrared light from a second LED mounted in the carriage housing;

receiving light from the LEDs which has traversed a blood oxygenated portion of a person with a photodiode integrally formed on a CMOS semiconductor chip mounted in the carriage housing and generating electrical signals; and on said CMOS semiconductor chip, digitizing the electrical signals from the photodiode and processing the digitized electrical signals into a blood oximetry value with an analog-to-digital converter and a processing circuit integrally formed on the CMOS semiconductor chip.

14. The method of measuring blood oxygen as set forth in claim 13, further including:

amplifying the electrical signals generated by the photodiode with an amplifier integrally formed on the CMOS semiconductor chip.

15. The medical pulse oximetry sensor as set forth in claim 1, wherein the carriage housing is formed as a single unit.

16. The medical pulse oximetry sensor as set forth in claim 1, wherein the CMOS chip embeds within the carriage housing.

17. A medical pulse oximetry sensor comprising:

a housing configured to fit a portion of a patient's anatomy with oxygenated blood throughput;

a first light emitting diode mounted in the housing, the first light emitting diode emitting light of a first spectrum;

a second light emitting diode mounted in the housing, the second light emitting diode emitting light of a second spectrum;

an integrated CMOS semiconductor component chip mounted in the housing and including integrally formed thereon:

a photodiode which detects light from the first and second light emitting diodes which has passed through the portion of the patient's anatomy, an amplifier which amplifies signals from the photodiode, an analog-to-digital converter which digitizes the amplified signals, and a light emitting diode controller which controls the first and second light emitting diodes.

18. The sensor as set forth in claim 17, wherein the CMOS semiconductor chip further includes:

a processor which processes the digitized signals into at least one of pulse oximetry values and plethymographic waveforms;

a timing circuit which coordinates the analog-to-digital converter, the processor, and the light emitting diode controller.

* * * * *